United States Patent [19]

Smiley

[11] 4,321,407
[45] Mar. 23, 1982

[54] TREATMENT OF DIBASIC ESTERS WITH ALKALI METAL BOROHYDRIDES

[75] Inventor: Robert A. Smiley, Wilmington, Del.

[73] Assignee: E. I. Du Pont de Nemours and Company, Wilmington, Del.

[21] Appl. No.: 169,734

[22] Filed: Jul. 17, 1980

[51] Int. Cl.$^3$ .................... C07C 67/62; C07C 67/60; C07C 69/40; C07C 69/42
[52] U.S. Cl. ................................. 560/191; 528/272; 560/198; 560/204; 562/530; 562/538
[58] Field of Search ...................... 560/191, 204, 190; 562/593, 530, 538

[56] References Cited

U.S. PATENT DOCUMENTS

| | | | |
|---|---|---|---|
| 2,197,546 | 4/1940 | Baxter et al. | 560/191 |
| 2,831,883 | 4/1958 | Hill et al. | 560/191 |
| 2,960,520 | 11/1960 | Brown et al. | 560/191 |
| 3,006,949 | 10/1961 | Brown et al. | 560/191 |
| 3,021,348 | 2/1962 | Kuceski | 560/191 |

Primary Examiner—Vivian Garner

[57] ABSTRACT

Process for reducing the color forming tendency of alkanedioic acid esters by contact with an alkali metal borohydride in the presence of water.

4 Claims, No Drawings

TREATMENT OF DIBASIC ESTERS WITH ALKALI METAL BOROHYDRIDES

BACKGROUND OF THE INVENTION

1. Field of the Invention

The present invention relates to reducing the color forming tendencies of certain esters and, more particularly, to the treatment of esters with an alkali metal borohydride in the presence of water.

2. Description of the Prior Art

Borohydrides are recognized as compounds for the selective reduction of a wide range of functional groups, e.g., aldehydes, ketones, imines, esters and amides, etc. The use of borohydrides is compiled in the publication entitled *Process Stream Purification,* Bulletin No. BA-8UG, Ventron Corp., Sept., 1978. This publication lists 6 patents relating to the purification of esters, but it does not include any relating to the removal of color formers from aliphatic dibasic esters.

U.S. Pat. No. 2,957,023 issued on Oct. 18, 1960 discloses a method for the stabilization of alcohols contaminated with carbonyl and/or unsaturated compounds such as olefins by adding a borohydride to the alcohol during or before the esterification. The patentees disclose that a solvent is preferred because of the relative insolubility of the borohydride but indicate that the choice of solvent is not critical to their invention. Solvents which are disclosed include water, isopropanol ether, low molecular weight amines and the like.

The production of color free polyvinyl alcohol is obtained according to the teachings of U.S. Pat. No. 3,679,646 issued on July 25, 1972 by pre-treating an alcohol solution of a polyvinyl ester with from about 0.03 to about 3% by weight based upon the weight of the polyvinyl ester of an alkali metal borohydride followed by alkaline hydrolysis. The patentees prefer to use the borohydride in a finely divided, e.g., powder form.

U.S. Pat. No. 3,681,482 issued on Aug. 1, 1972 discloses a process for improving the color of phosphate esters by contacting the esters with 0.002 to 0.05 percent by weight of sodium or lithium borohydride. The patentees disclose that the borohydride is preferably in solid form but can be in aqueous solution.

German Pat. No. 2,556,258 issued on May 26, 1977 teaches the stabilization of polyhydroxy carboxylate polymers by the addition of sodium borohydride.

U.S. Pat. No. 3,991,100 issued on Nov. 9, 1976 discloses a process for the production of esters of dibasic acids which exhibit a reduced color-forming tendency under alkaline or transesterification conditions. The process involves heating the esters to remove water, oxides of nitrogen and nitric acid, esterifying the thus heated product and finally distilling off volatile materials in the presence of a dry base such as sodium carbonate and calcium hydroxide. It should be noted, however, that this method does not completely eliminate the color-forming tendencies of the esters during transesterification.

The art discloses that under ordinary conditions aliphatic nitro compounds are not reactive with sodium borohydride and that for such a reaction to occur to any significant extent transition metals, their salts and complexes of Lewis acids are required (*Sodium Borohydride,* Ventron Corporation, Dec., 1979 pages 35-36).

SUMMARY OF THE INVENTION

A process for reducing the color forming tendency of alkanedioic acid esters, e.g., those esters derived from dicarboxylic acids having 4–12 carbon atoms which comprises contacting the esters with alkali metal borohydride, preferably sodium borohydride, in the presence of water. It is preferred to dissolve the borohydride in water before contact with the esters.

DETAILED DESCRIPTION OF THE INVENTION

The esters to which the present invention is particularly applicable are those prepared from the acids isolated as co-products from the air oxidation of cyclic hydrocarbons to cyclic ketones and alcohol followed by the oxidation of the ketones and alcohols with nitric acid. The oxidation of cyclohexane to cyclohexanol and cyclohexanone can be conducted according to the teachings, for example, of U.S. Pat. No. 3,530,185 issued on Sept. 22, 1970. Cyclohexanol and cyclohexanone produced according to the aforementioned patent are then oxidized with nitric acid according to the teachings of U.S. Pat. Nos. 3,359,308 issued on Dec. 19, 1967 and 3,365,490 issued on Jan. 23, 1968. Illustrative of the co-product acids that are produced along with adipic acid in the aforementioned processes are succinic acid and glutaric acid.

The preparation of alkane dicarboxylic acids having from 8 to 12 carbon atoms by the nitric acid oxidation of the corresponding alcohols and ketones is disclosed in U.S. Pat. No. 3,758,564 issued on Sept. 11, 1973. Illustrative of the co-product acids produced in this process are pimelic acid, suberic acid, azelaic acid, sebacic acid and undecanedioic acid.

The principle acids produced in the above described processes, i.e., adipic acid and dodecanedioic acid are commonly separated from the co-product acids by crystallization and the co-product acids then recovered from the mother liquor by known methods. These co-product acids can be converted to esters by known esterification processes. Even after rigorous distillation, these esters still exhibit a marked tendency to turn yellow when subjected to alkaline conditions or when heated to temperatures for which the esters are eventually employed, e.g., for the preparation of other esters and polyesters by transesterification.

The color-forming tendency of esters which are treated according to the process of the present invention is believed due to the presence of small amounts of aliphatic nitro compounds which form during the nitric acid oxidation of the ketones or alcohols and/or during acid catalyzed esterification in the presence of residual nitrate ion. These impurities co-distill with the esters; are not adsorbed to any significant extent on activated carbon and are not amenable to bleaching, e.g., with peroxides or aqueous hypochlorites.

The borohydrides which are operable in the present invention include sodium, potassium and lithium borohydride and mixtures of the foregoing. Sodium borohydride is the preferred borohydride.

The method for contacting the borohydride with the esters is not critical to the present invention provided water is present during contact. Low shear stirring at ambient temperature has been found completely satisfactory for mixing, but as one skilled in the art can appreciate, higher shear mixing and/or elevated temperatures will accelerate the reaction. The contacting may be conducted at temperatures in the range of 0°–100° C. and preferably 20°–75° C. for times varying from about 0.5–2 hours. Time can be decreased as the agitation and/or temperature is increased. The borohydride and water may be introduced separately into the esters but preferably, the borohydride is dissolved in water before introduction. The minimum amount of water required for formation of the solution depends on the solubility of the borohydride at the temperature of the water, but the amount of water can be up to twice the weight of the borohydride or more. It is desirable to introduce only the minimum amount of water necessary and thereby minimize the drying required after reaction.

Since the borohydrides decompose rapidly in the presence of acid, the esters should be neutral or slightly basic for optimum utilization of the hydride and for color reduction.

The amount of borohydride required will, of course, depend upon the amount of color-formers present which is dictated by the conditions used in preparing the acids and/or the esters. It has been determined that two parts by weight of borohydride per 1000 parts by weight of ester is usually sufficient for complete reduction in color. However, in many instances less than one part of borohydride per 1000 parts of ester can accomplish complete color reduction. Generally, 0.05–5% and preferably about 0.1–0.3% by weight of borohydride based upon the weight of the ester is employed. In any event, the amount of borohydride required is readily determined by increasing or decreasing the amount of borohydride until the desired level of color is obtained. Excess borohydride can be employed to assure an essentially complete reduction in color forming tendency.

The following examples are presented to illustrate but not to restrict the present invention. Parts and percentages are by weight unless otherwise specified. The color forming tendencies of the esters treated according to the process of the present invention were determined by adding two drops of a 40% by weight solution of benzyltrimethyl ammoniumhydroxide in methanol to 5 ml of esters, followed by shaking the solution. All esters reported in the Examples were treated in this manner before determining the color. The polyesters were not treated before determining the color. Color was judged using a Hellige Color Comparator equipped with a Gardner color disc (color system of the Institute of Paint and Varnish Research). This technique measures the yellowness of samples on a scale from 1 (very light yellow) to 10 (dark yellow). A colorless sample exhibits a Gardner color of less than 1.

EXAMPLE 1

To a 12 liter flask fitted with a simple distillation head and suitable heating equipment was added 10 kilograms of the mixed methyl esters of succinic, glutaric and adipic acid, having the analysis set forth in Table I and a Gardner color of 6.

TABLE I

| Dimethyl succinate | 2% |
|---|---|
| Dimethyl glutarate | 71% |
| Dimethyl adipate | 27% |

This ester mixture was prepared as described hereinabove by esterification of the acids obtained by the nitric acid oxidation of a mixture of cyclohexanol and cyclohexanone followed by removal of the majority of adipic acid by crystallization.

Approximately 10 grams of sodium borohydride was dissolved in 20 grams of water and the resultant solution introduced into the flask. After standing overnight at room temperature (about 16 hours at 20° C.), the ester had a Gardner number less than 1. This ester was then distilled under 25 mm Hg vacuum. A small foreshot was removed and 9.5 kilograms of distillate at a boiling point in the range of 110°–118° C. was collected. The distillate also exhibited a Gardner color of less than 1 and when a polyester was made from this material by transesterification with ethylene glycol in the presence of n-butyl stannoic acid, a polyester having a Gardner color of less than 1 was obtained.

COMPARATIVE A

Example I was repeated except that 10 grams of powdered sodium borohydride (no water) were thoroughly mixed with the esters. The Gardner color of the distillate was 4 indicating that only a small amount of color-formers were removed in the absence of water.

COMPARATIVE B

Example I was repeated except that 40 grams of sodium borohydride (no water) were employed. A polyester prepared from this ester had a Gardner color of 6.

The foregoing illustrates that even a substantial excess of sodium borohydride does not provide satisfactory color reduction in the absence of water.

EXAMPLE II

A mixture of $C_{7-12}$ straight chain dibasic acids recovered from the nitric acid oxidation of cyclododecanone and cyclododecanol as described hereinabove were esterified with methanol using a dodecylbenzene sulfonic acid catalyst. The resultant esters were then distilled under 1 mm Hg pressure and a distillate boiling in the range of 99°–150° C. and having a Gardner color of 7 was recovered. This ester distillate had the composition given in Table II.

TABLE II

| Dimethyl pimelate | 0.5% | Dimethyl sebacate | 7.0% |
|---|---|---|---|
| Dimethyl suberate | 2.4% | Dimethyl undecandioate | 47.6% |
| Dimethyl azelate | 3.3% | Dimethyl dodecandioate | 39.2% |

To 150 parts of this ester distillate was added 6 parts of a 25% by weight aqueous solution of sodium borohydride. The mixture was then stirred at room temperature for 1 hour and then re-distilled under the above described conditions. A small foreshot boiling below 99° C. was taken and discarded. A product was collected at a boiling range of 99°–155° C. which has a Gardner color of less than 1.

I claim:

1. A method of reducing the color-forming tendency of esters obtained by esterifying alkanedioic acids having 4–12 carbon atoms which acids are produced by the nitric acid oxidation of cycloaliphatics selected from the class consisting of ketones, alcohols and mixtures of the foregoing which method comprises contacting said esters with an alkali metal borohydride in the presence of water and thereafter recovering the thus treated esters.

2. The process of claim 1 wherein the borohydride is sodium borohydride.

3. The process of claim 1 wherein the borohydride is dissolved in the water before contact with the ester.

4. The process of claim 3 wherein the borohydride is sodium borohydride.